United States Patent [19]

Cavazza et al.

[11] Patent Number: 5,418,253
[45] Date of Patent: May 23, 1995

[54] ESTERS OF L-CARNITINE AND ALKANOYL L-CARNITINES WITH GLYCOLIC ACID OR ESTERS THEREOF AND PHARMACEUTICAL COMPOSITIONS CONTAINING SAME FOR TREATING DERMATOSES

[75] Inventors: Claudio Cavazza; Paolo Cavazza, both of Rome, Italy

[73] Assignee: Avantgarde S.p.A., Rome, Italy

[21] Appl. No.: 280,663

[22] Filed: Jul. 27, 1994

Related U.S. Application Data

[63] Continuation of Ser. No. 138,103, Oct. 20, 1993, abandoned.

[30] Foreign Application Priority Data

Oct. 20, 1992 [IT] Italy ............................. RM92A0761

[51] Int. Cl.$^6$ ........................................... A61K 31/225
[52] U.S. Cl. ...................... 514/547; 514/561; 560/170; 562/567
[58] Field of Search ................. 560/170; 562/567; 514/547, 561

[56] References Cited

U.S. PATENT DOCUMENTS

| | | | |
|---|---|---|---|
| 4,439,438 | 3/1984 | Cavazza | 424/263 |
| 4,443,475 | 4/1984 | Cavazza | 560/170 |
| 4,743,621 | 5/1988 | Cavazza | 514/547 |
| 5,246,967 | 9/1993 | Zezza | 514/547 |

FOREIGN PATENT DOCUMENTS

| | | |
|---|---|---|
| 902796 | 7/1985 | Belgium . |
| 903270 | 3/1986 | Belgium . |
| 429403 | 5/1991 | European Pat. Off. . |
| 442850 | 8/1991 | European Pat. Off. . |
| 443996 | 8/1991 | European Pat. Off. . |
| 8502578 | 4/1987 | Netherlands . |

*Primary Examiner*—José G. Dees
*Assistant Examiner*—Samuel Barts
*Attorney, Agent, or Firm*—Oblon, Spivak, McClelland, Maier & Neustadt

[57] ABSTRACT

Ester of L-carnitine and alkanoyl L-carnitines with glycolic acid and esters thereof are disclosed, which are formulated into topically applicable pharmaceutical compositions for the treatment of dermatoses.

6 Claims, No Drawings

ESTERS OF L-CARNITINE AND ALKANOYL L-CARNITINES WITH GLYCOLIC ACID OR ESTERS THEREOF AND PHARMACEUTICAL COMPOSITIONS CONTAINING SAME FOR TREATING DERMATOSES

This application is a continuation of application Ser. No. 08/138,103, filed on Oct. 20, 1993, now abandoned.

The present invention relates to esters of L-carnitine and alkanoyl L-carnitines with glycolic acid or esters of glycolic acid and pharmaceutical compositions which contain such esters as active ingredients, suitable to be topically applied for the treatment of dermatoses.

The esters of the present invention have the general formula (I)

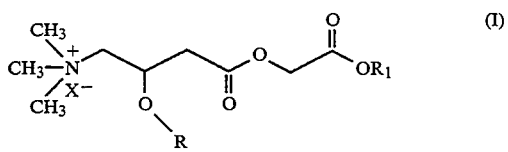

wherein:

R is hydrogen or a straight or branched alkanoyl group having 2-5 carbon atoms;

$R_1$ is hydrogen or a straight or branched alkyl group having 1-4 carbon atoms; and $X^-$ is the anion of a pharmacologically acceptable salt.

Encompassed by the compounds of the present invention are also the inner salts of the compounds of the general formula (I), having the general formula (I')

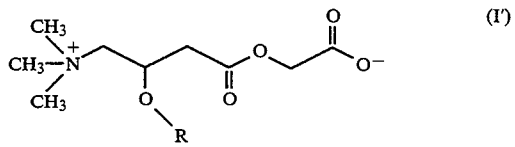

If R is an alkanoyl, it is preferably selected from acetyl, propionyl, butyryl, isobutyryl, valeryl and isovaleryl.

If $R_1$ is an alkyl, it is preferably selected from methyl, n-butyl and tert-butyl.

Pharmaceutically acceptable salts of the compound of formula (I) include, in addition to the inner salts, all pharmaceutically acceptable salts which are prepared by the addition of acid to L-carnitine, and which do not give rise to undesirablie toxic or collateral effects. The formation of pharmaceutically acceptable acid addition salts is well known in pharmaceutical techonology.

Non-limiting examples of suitable salts include the chloride, bromide, orotate, acid aspartate, acid citrate, acid phosphate, fumarate, acid fumarate, lactate, maleate, acid maleate, acid oxalate, acid sulfate, glucose phosphate, tartrate and acid tartrate salts.

The dermatoses which are suitably treated with the compositions of the present invention are in particular ichthyosis, psoriasis and those dermatoses which are induced by a defective keratinization, such as dandruff, acne and palmar and plantar hyperkeratosis.

Ichthysosis is a dermatosis characterized by generalized dryness, harshness and scaling of the skin. It may occur as a hereditary disease present at birth, or as a metabolic disorder associated with hypothyroidism or with the intake of drugs (such as butyrophenols) inhibiting lipid synthesis, or as a paraneoplastic syndrome, manifestation of a tumor process involving internal organs.

Xeroderma, the mildest form of ichthyosis is neither congenital nor associated with systemic abnormalities.

It usually occurs on the lower legs of middle-aged or older patients, most often in cold weather and in patients who bathe frequently. There may be mild to moderate itching and an associated dermatitis due to detergents or other irritants.

The inherited ichthyoses, all characterized by excessive accumulation of scale on the skin surface, are classified according to clinical, genetic, and histologic criteria.

Known treatments of any form of ichthyosis comprise topically applying to the skin hydrating emollients. Furthermore, salicylic acid or vitamin A-containing ointments have been widely used.

A keratolytic agent particularly effective in removing the scale in ichthyosis vulgaris, lameliar ichthyosis and sex-linked ichthyosis contains 6% salicylic acid in a gel composed of propylene glycol, ethyl alcohol, hydroxypropylene cellulose and water.

Further known drugs for the treatment of this disorder include: 50% propylene glycol in water, hydrophilic petrolatum and water (in equal parts), and cold cream and an α-hydroxy acid (e.g. lactic and pyruvic acid) in various bases. In lameliar ichthyosis, 0.1% tretinoin (vitamin A acid; retinoic acid) cream has been utilized.

None of these treatments has been found satisfactorily effective.

Hyperkeratosis is a thickening of the stratum corneum of the skin. The treatment of choice is the topical application of drugs containing urea, propylene glycol or salicylic acid. Also in this case, none of the known treatment has proved to be satisfactorily effective.

It has now been found that the compounds of the present invention, when topically applied as solutions, lotions, creams or ointments containing from 0.01% to 20%, preferably from 1% to 15% and most preferably from 2 to 10% by weight of a least one of the foregoing compounds, are potently effective in achieving complete remission of ichthyotic conditions in humans and in healing psoriasis and those disorders brought about by an altered keratinization, such as dandruff, acne and palmar and plantar hyperkeratosis.

It has also been found that, if the solutions, creams or ointments of the invention are applied regularly on a daily basis, within about two to three weeks the effected skin areas will return to norm conditions.

The compounds of formula (I) are prepared via a process whose steps are illustrated in the following reaction scheme, wherein R, $R_1$ and $X^-$ have the previously defined meanings.

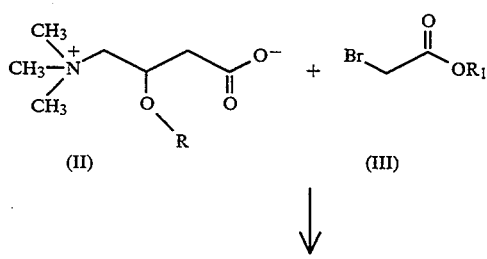

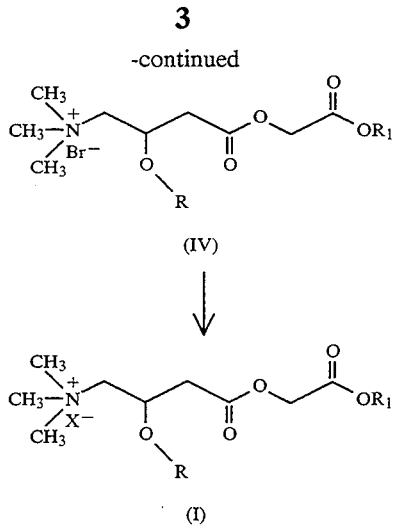

More specifically, carnitine or the alkanoylcarnitine inner salt (II) is reacted with a bromoacetic acid ester (III) in an organic aprotic solvent, such as dimethylformamide, tetrahydrofurane or acetonitrile, at 20° C.–40° C., for 2–24 hours.

The reaction product is precipitated with ethyl ether, filtered off and dried under vacuum.

The bromide (IV) thus obtained is optionally converted to $X^-$ salt, by eluting the bromide through a column of a strongly basic ion exchange resin such as AMBERLITE IRA 402 activated in $HCO^-_3$ form and adding the stoichiometric amount of the pharmacologically acceptable acid HX to the eluate aqueous solution, or by eluting the bromide through a column of a strongly basic ion exchange resin such as IRA 402 activated in $X^-$ form.

In either case, the solid product, salified with $X^-$, is obtained by lyophilization.

If the inner salts of the formula (I') are desired, the suitable tert-butyl ester, e.g. the compound of Example 1 (ST 777), is kept under stirring in trifluoroacetic acid or in a mixture of trifluoroacetic acid and methylene chloride at room temperature for one hour or in a 30% solution of anhydrous hydrobromic acid in acetic acid.

The solution is concentrated to dryness under reduced pressure, the residue is taken up with water and the resulting solution eluted through a strongly anionic resin (e.g. IRA 402) activated in bicarbonate form.

The inner salt is obtained by lyophilizing the eluate.

The following non-limiting examples show the preparation and the physico-chemical properties of some compounds of the invention.

EXAMPLE 1

Preparation of the ester of L-carnitine bromide with tert-butylglycolate (ST 777). 10.9 g (0,055 moles) of tert-butylbromoacetate (M.W. 195,06) were added dropwise under stirring to a suspension of 8.06 g (0,05 moles) of L-carnitine inner salt (M.W. 161,2) in 15 mL of anhydrous dimethylformamide, while keeping the temperature at 25° C.

The reaction was monitored via TLC (eluant $CHCl_3$:MeOH:$H_2O$: IsoPrOH:AcOH 60:40:15:10:15).

After stirring for 5 hours at 25° C., the resulting thin suspension was filtered and the flitrate slowly added dropwise under vigorous stirring to 1 L ethyl ether.

The supernatant ether solution was removed and the thick oil which separated was treated with 500 mL ethyl ether under vigorous stirring for one hour, at 25° C., resulting into a crystalline precipitate.

The precipitate was quickly filtered and the residual solvent removed at 35° C. under reduced pressure. 15 g of the title compound (M.W. 356,26) were obtained as a colourless solid. Yield 84.2%.

M.P. 100°–101° C.

$[\alpha]^{25}_D = -10.3°$ (C=1 in $H_2O$)

TLC: single spot (eluant $CHCl_3$:MeOH:isoPrOH:AcOH 60:40:15:10:15)

Silica gel plates 0.25 mm-60$F_{254}$ (E. Merck)

Detectors U.V.$\lambda$.=254 nm and iodine vapours

Elementary Analysis ($C_{13}H_{26}BrNO_5$) M.W. 356.26

| calc. % | C 43.88 | H 7.36 | Br 22.43 | N 3.93 |
|---|---|---|---|---|
| found. % | C 43.77 | H 7.44 | Br 22.35 | N 3.78 |
| HPLC Waters: | spherisorb column RP1 (5µ), inner diameter = 4 mm length = 125 mm mobile phase $KH_2PO_4$ 0.05M/$CH_3CN$ 60:40, t = 25° C. flow rate: 1 ml/min detector R.I. mod 410 capacity factor ($K^1$) calculated on the Br— anion peak, $K^1 = 0,94$ | | | |

$^1$H-NMR:

Varian 300 MHz ($CDCl_3$) $\delta$ (p.p.m.): 1.43 (9H,s,C($CH_3$)$_3$);

2.70–2.94 (2H, m, $CH_2COO$); 3.49 (9H,s,$^+N(CH_3)_3$);

3.66–3.87 (2H,m,$CH_2N$); 4.52 (2H, sist. AB, O$CH_2COO$);

4.78 ($^1$H,m,CHOH).

EXAMPLE 2

Preparation of the ester of acetyl L-carnitine bromide with tert-butyl glycolate (ST 766).

The title compound was prepared as described in Example 1, utilizing acetyl L-carnitine inner salt.

Pysico-chemical properties.

M.P.=131°–133° C.

$[\alpha]^{25}_D = -16,8°$ (C=1 in $H_2O$)

TLC: as in Example 1

Elementary analysis ($C_{15}H_{28}BrNO_6$) M.W. 398.30

| calc. % | C 45.23 | H 7.09 | Br 20.06 | N 3.52 |
|---|---|---|---|---|
| found % | C 45.05 | H 7.18 | Br 19.91 | N 3.49 |
| HPLC: Waters: | spherisorb column RP1 (5µ), inner diameter = 4 mm length 125 mm mobile phase $KH_2PO_4$ 50 mm/$CH_3CN$ 60:40, t = 25° C. flow rate: 1 ml/min detector R.I. mod 410 capacity factor ($K^1$) calculated on the Br— anion peak, $K^1 = 1,50$ | | | |

$^1$H-NMR:

Varian 300 MHz ($CDCl_3$) $\delta$ (p.p.m.): 1.43 (9H,s,C($CH_3$)$_3$);

2.16 (3H, s, $CH_3COO$); 2.93 (2H,m, $CH_2COO$); 3.35 (9H,s,N ($CH_3$)$_3$);

4.12–4.33 (2H,m,$CH_2N$); 4.55 (2H,sist.AB,O$CH_2COO$);5.72 (1H,m,CHOCO).

EXAMPLE 3

Preparation of the ester of propionyl L-carnitine bromide with tert-butyl glycolate (ST 788).

The title compound was prepared as described in Example 1, utilizing propionyl L-carnitine inner salt.
Physico-chemical properties.
M.P.=130°–132° C.
$[\alpha]^{25}_D = -19.8°$ (C=1 in H$_2$O)
TLC: as in Example 1.
Elementary analysis (C$_{16}$H$_{30}$BrNO$_6$) M.W. 412.33

| calc. % | C 46.61 | H 7.33 | Br 19.38 | N 3.40 |
|---|---|---|---|---|
| found % | C 46.49 | H 7.35 | Br 19.50 | N 3.33 |
| HPLC Waters: | spherisorb column RP1-(5μ), inner diameter = 4 mm length = 125 mm mobile phase KH$_2$PO$_4$ 50 mM/CH$_3$CN 35:65, t = 25° C. flow rate: 1 ml/min detector R.I. mod 410 capacity factor (K$^1$) calculated on the Br— anion peak, K$^1$ = 0,79 | | | |

$^1$H-NMR:
Varian 300 MHz (CDCl$_3$) δ (p.p.m.): 1.14 (3H,s,CH$_2$CH$_3$);
1.46 (9H,s,C(CH$_3$)$_3$); 2.42 (2H,q,CH$_2$CH$_3$); 2.95 (2H,d,CH$_2$COO);
3.55 (9H,s,+N(CH$_3$)$_3$) 4.12–4.38 (2H,m,CH$_2$N);
4.55 (2H,sist.AB,OCH$_2$COO); 5.73(1H,m,CHOCO).

EXAMPLE 4

Preparation of the ester of isobutyryl L-carnitine bromide with tert-butyl glycolate (ST 779).

The title compound was prepared as described in Example 1, ultilizing isobutyryl L-canitine inner salt.
Physico-chemical properties.
M.P.=121°–123° C.
$[\alpha]^{25}_D = -17,4°$ (C=1 in H$_2$O)
TLC: as in Example 1.
Elementary analysis (C$_{17}$H$_{32}$BrNO$_6$) M.W. 426.36

| calc. % | C 47.89 | H 7.57 | Br 18.74 | N 3.29 |
|---|---|---|---|---|
| found % | C 47.70 | H 7.65 | Br 18.76 | N 3.15 |
| HPLC Waters: | spherisorb column RP1 (5μ), inner diameter = 4 mm length = 125 mm mobile phase KH$_2$PO$_4$ 50 mM/CH$_3$CN 35:65, t = 50° C. flow rate: 1 ml/min detector R.I. mod 410 capacity factor (K$^1$) calculated on the Br— anion peak, K$^1$ = 0,90 | | | |

$^1$H-NMR:
Varian 300 MHz (CDCl$_3$) δ (p.p.m.): 1.18 (6H,d,CH(CH$_3$)$_2$);
1.46 (9H,s,C(CH$_3$)$_3$); 2.62 (1H,m,CH(CH$_3$)$_2$); 2.90 (2H,m,CH$_2$COO);
3.55 (9H,s,+N(CH$_3$)$_3$) 4.15–4.35 (2H,m,CH$_2$ N) ;
4.57 (2H,sist.AB,OCH$_2$COO); 5.73(1H,m,CHOCO).

EXAMPLE 5

Preparation of the ester of isovaleryl L-carnitine bromide with tert-butyl glycolate (ST 767).
The title compound was prepared as described in Example 1, utilizing isovaleryl L-carnitine inner salt.
M.P.=136°–137° C.
$[\alpha]^{25}_D = -16,3°$ (C=1 in H$_2$O)
TLC: as in Example 1.
Elementary analysis (C$_{18}$H$_{34}$BrNO$_6$) M.W. 440.38

| calc. % | C 49.09 | H 7.78 | Br 18.15 | N 3.18 |
|---|---|---|---|---|
| found % | C 49.19 | H 7.90 | Br 18.20 | N 3.00 |
| HPLC Waters: | spherisorb column RP1 (5μ), inner diameter = 4 mm length 125 mm mobile phase KH$_2$PO$_4$ 50 mM/CH$_3$CN 60:40, t = 25° C. flow rate: 1 ml/min detector R.I. mod 410 capacity factor (K$^1$) calculated on the Br— anion peak, K$^1$ = 3,43 | | | |

$^1$H-NMR:
Varian 300 MHz (CDCl$_3$) δ (p.p.m.): 0.93 (6H,d,CH(CH$_3$)$_2$);
1.47 (9H,s,C(CH$_3$)$_3$); 2.09 (1H,m,CH(CH$_3$)$_3$); 2.26 (2H,m,CH$_2$CH);
2.93 (2H,m,CH$_2$COO) 3.55 (9H,s,+N(CH$_3$)$_3$)-4.10–4.33(2H,m,CH$_2$N);
4.55 (2H,sist.AB,OCH$_2$COO); 5.73(1H,m,CHOCO).

EXAMPLE 6

Preparation of the ester of L-carnitine bromide with metyl glycolate (ST 839).

17.93 (0.117 moles) of metyl bromoacetate (M.W. 152.98) were added dropwise unter stirring to a suspension of 17 g (0.105 moles) of L-carnitine inner salt (M.W. 161.2) in 40 mL of anhydrous dimethylformamide while keeping the temperature at 25° C.

The reaction was monitored via TLC (eluant CHCl$_3$:MeOH:H$_2$O:IsoPrOH:AcOH 60:40:15:10:15).

After stirring for 3 hours at 25° C., the remaining thin suspension was filtered and the flitrate added dropwise under vigorous stirring to 1.5 L of ethyl ether.

A precipitate was obtained, which was filtered off and suspended in 500 mL of ethyl ether for one hour under vigorous stirring, filtered off once more and dried at 35° C. under reduced pressure.

32 g of the title compound (M.W. 314.18) were obtained as a colourless solid. Yield 97%.
Phisico-chemical properties
M.P.=156°–160° C.
$[\alpha]^{25}_D = -10,2°$ (C=1 in H$_2$O)
TLC: as in Example 1.
Elementary analysis (C$_{10}$H$_{20}$BrNO$_5$) M.W. 314.18

| calc. % | C 38.23 | H 6.42 | Br 25.43 | N 4.46 |
|---|---|---|---|---|
| found % | C 38.45 | H 6.53 | Br 25.27 | N 4.60 |
| HPLC Waters: | spherisorb column-C1 (5 μm), inner diameter = 4 mm length = 125 mm mobile phase KH$_2$PO$_4$ 50 mM/CH$_3$CN 90:10, t = 40° C. flow rate: 0,5 ml/min detector R.I. mod 410 capacity factor (K$^1$) calculated on the Br— anion peak, K$^1$ = 0,45 | | | |

$^1$H-NMR:
Varian 300 MHz (D$_2$O) δ (p.p.m.): 2.75–2.90 (2H,M,CH$_2$COO);
3.25 (9H,s,+N(CH$_3$)$_3$); 3.50–3.60 (2H,m,CH$_2$N); 3.82 (3H,s,OCH$_3$);
4.73 (2H,s,OCH$_2$COO); 4.80 (1H,s,CHOH).

EXAMPLE 7

Preparation of the ester of acetyl L-carnitine bromide with methyl glycolate (ST 845).

The title compound was prepared as described in Example 6, utilizing acetyl L-carnitine inner salt.
Physico-chemical properties.
$[\alpha]^{25}_D = -18{,}2°$ (C=1 in $H_2O$)
TLC: as in Example 1.
Elementary analysis ($C_{12}H_{22}BrNO_6$) M.W. 356.22

| calc. % | C 40.46 | H 6.23 | Br 22.43 | N 3.93 |
|---|---|---|---|---|
| found % | C 40.35 | H 6.31 | Br 22.35 | N 4.01 |
| HPLC Waters: | spherisorb column-Cl (5μ), inner diameter = 4 mm length = 125 mm mobile phase $KH_2PO_4$ 50 mM/$CH_3CN$ 90:10, t = 40° C. flow rate: 0.5 ml/min detector R.I. mod 410 capacity factor ($K^1$) calculated on the Br— anion peak, $K^1$ = 0,72 | | | |

$^1$H-NMR:
Varian 300 MHz ($D_2O$) δ (p.p.m.): 2.18 (3H,s,$CH_3COO$);
3.02 (2H,m,$CH_2COO$; 3.22 (9H,s,$^+NCH_3)_3$); 3.69–4.02 (2H,m,$CH_2N$);
3.82 (3H,s,$OCH_3$); 4.80 (2H,s,$OCH_2COO$); 5.70 (1H,m,$CHOCOCH_3$).

EXAMPLE 8

Preparation of the ester of propionyl L-carnitine bromide with methyl glycolate (ST 935).

The title compound was prepared as described in Example 6, utilizing propionyl L-carniitne inner salt.
Physico-chemical properties
M.P.=107°–110° C.
$[\alpha]^{25}_D = -21{,}5°$ (C=1 in $H_2O$)
TLC: as in Example 1.
Elementary analysis ($C_{13}H_{24}BrNO_6$) M.W. 370.25

| calc. % | C 42.17 | H 6.53 | Br 21.58 | N 3.78 |
|---|---|---|---|---|
| found % | C 41.98 | H 6.63 | Br 21.42 | N 3.79 |
| HPLC Waters: | spherisorb column Cl (5μ), inner diameter = 4 mm length 125 mm mobile phase $KH_2PO_4$ 50 mM/$CH_3CN$ 90:10, t = 50° C. detector R.I. mod 410 capacity factor ($K^1$) calculated on the Br— anion peak, $K^1$ = 1,28 | | | |

$^1$H-NMR:
Varian 300 MHz ($D_2O$) δ (p.p.m.): 1.12 (3H,s,$CH_3CH_2$);
2.48 (2H,q,$CH_3CH_2$; 3.02 (2H,d,$CH_2COO$); 3.22 (9H,s,$^+N CH_3)_3$);
3.70–4.02 (2H,m,$CH_2N$); 3.81 (3H,s,$OCH_3$); 4,80 (2H,d,$OCH_2COO$);
5.74 (1H,m,$CHOCO$).

EXAMPLE 9

Preparation of the ester of isobutyryl L-carnitine bromide with methyl glycolate (ST 846).

The title compound was prepared as described in Example 6, utilizing isobutyryl L-carnitine inner salt.
Physico-chemical properties.
M.P.=98°–102° C.
$[\alpha]^{25}_D = -19{,}1°$ (C=1 in $H_2O$)
TLC: as in Example 1.
Elementary analysis ($C_{14}H_{26}BrNO_6$) M.W. 384.28

| calc. % | C 43.76 | H 6.82 | Br 20.79 | N 3.64 |
|---|---|---|---|---|
| found % | C 43.90 | H 6.71 | Br 20.65 | N 3.65 |
| HPLC Waters: | spherisorb column Cl (5 μm), inner diameter = 4 mm length = 125 mm mobile phase $KH_2PO_4$ 50 mM/$CH_3CN$ 80:20, t = 40° C. flow rate: 0,5 ml/min detector R.I. mod 410 capacity factor ($K^1$) calculated on the Br— anion peak, $K^1$ = 1,04 | | | |

$^1$H-NMR:
Varian 300 MHz ($D_2O$) δ (p.p.m.): 1.15 (6H,d,$(CH_3)_2CH$);
2.68 (1H,m,$CH(CH_3)_2$); 3.00 (2H,d,$CH_2COO$); 3.22 (9H,s,$^+N(CH_3)_3$);
3.70–403 (2H,m,$CH_2N$); 3,79 (3H,s,$OCH_3$); 4.77 (2H,s,$OCH_2COO$);
5.73 (1H,m,$CHOCO$).

EXAMPLE 10

Preparation of the ester of isovaleryl L-carnitine bromide with methyl glycolate (ST 936).

The title compound was prepared as described in Example 6, utilizing isovaleryl L-carnitine inner salt.
Physico-chemical properties.
$[\alpha]^{25}_D = -17{,}2°$ (C=1 in $H_2O$)
TLC: as in Example 1.
Elementary analysis ($C_{15}H_{28}BrNO_6$) M.W. 398.30

| calc. % | C 45.23 | H 7.09 | Br 20.06 | N 3.52 |
|---|---|---|---|---|
| found % | C 45.10 | H 7.07 | Br 19.95 | N 3.57 |
| HPLC Waters: | spherisorb column-Cl (5 μm), inner diameter = 4 mm length = 125 mm mobile phase $KH_2PO_4$ 50 mM/$CH_3CN$ 90:10, t = 50° C. flow rate: 0,5 ml/min detector R.I. mod 410 capacity factor ($K^1$) calculated on the Br— anion peak, $K^1$ = 2,42 | | | |

$^1$H-NMR:
Varian 300 MHz ($D_2O$) δ (p.p.m.): 0.93 (6H,d,$(CH_3)_2CH$);
2.05 (1H,m,$CH(CH_3)_2$); 2.35 (2H,m,$CH_2CH$); 3.02 (2H,d,$CH_2COO$);
3.22 (9H,s,$^+N(CH_3)_3$); 3.70–4.02 (2H,m,$CH_2N$) 3.80 (3H,s,$OCH_3$);
4.78 (2H,m,O $CH_2COO$); 5.75 (1H,m,$CHOCO$).

EXAMPLE 11

Preparation of the ester of L-carnitine bromide with n-butyl glycolate (ST 761).

9.08 g (0.0465 moles) of n-butyl bromoacetate, M.W. 195.05 (Arthur I. Vogel J.C.S. 648, 1948) were added dropwise under stirring to a suspension of 6.99 g (0.0433 moles) of L-carnitine inner salt (M.W. 161.2) in 10 mL of anhydrous dimethylformamide, while keeping the temperature at 25° C.

The reaction was monitored via TLC (eluant $CHCl_3$:MeOH:$H_2O$:isoPrOH 60:40:15:10:15).

Following stirring for 3 hours at 25° C., the remaining thin suspension was filtered and the flitrate slowly added dropwise to 1 L ethyl ether under vigorous stirring.

The suspension thus formed was kept under stirring at 25° C. for 2 hours and then kept at 5° C. overnight.

The ether solution was removed and the oil which formed treated under vigorous stirring with ethyl ether which was then removed. The oily residue was then dried at 35° C. under reduced pressure.

The product thus obtained was then lyophilized, yielding 13 g of the title compound (M.W. 356.26) as a colourless pitchy solid. Yield 84.3%.

$[\alpha]^{25}_D = -11.0°$ (C=1 in $H_2O$)

TLC: as in Example 1.

Elementary analysisis ($C_{13}H_{26}BrNO_5$) M.W. 356.26

| calc. % | C 43.83 | H 7.36 | Br 22.43 | N 3.93 |
|---|---|---|---|---|
| found % | C 43.95 | H 7.55 | Br 22.37 | N 3.76 |
| HPLC Waters: | spherisorb column-RP1 (5μ), inner diameter = 4 mm length = 125 mm mobile phase $KH_2PO_4$ 50 mM/$CH_3CN$ 60:40, t = 25° C. flow rate: 1 ml/min detector R.I. mod 410 capacity factor ($K^1$) calculated on the Br— anion peak, $K^1$ = 0,83 | | | |

$^1$H-NMR:

Varian 300 MHz ($CDCl_3$) (p.p.m.): 0.94 (3H,t,$CH_2CH_3$);

1.48 (2H,m,$CH_2CH_3$); 1.64 (2H,m,$CH_2$ $CH_2CH_2$);

2.76–2.96 (2H,m,$CH_2COO$); 3.49 (6H,s,+N($CH_3)_3$); 3.70–3.90 (2H,m,$CH_2N$);

4.15 (2H,t,$OCH_2CH_2$); 4.67 (2H,sist.AB,$OCH_2COO$); 4.85 (1H,s,CHOH).

EXAMPLE 12

Preparation of acetyl L-carnitine bromide with n-butyl glycolate (ST 799).

The title compound was prepared as described in Example 11, utilizing acetyl L-carnitine inner salt.

Physico-chemical properties.

$[\alpha]^{25}_D = -14.7°$ (C=1 in $H_2O$)

TLC: as in Example 1.

Elementary analysis ($C_{15}H_{28}BrNO_6$) M.W. 398.30

| calc. % | C 45.23 | H 7.09 | Br 20.06 | N 3.52 |
|---|---|---|---|---|
| found % | C 45.15 | H 7.13 | Br 19.98 | N 3.60 |
| HPLC Waters: | spherisorb column-C1 (5μ), inner diameter = 4 mm length = 125 mm mobile phase $KH_2PO_4$ 50 mM/$CH_3CN$ 70:30, t = 35° C. flow rate: 0,5 ml/min detector R.I. mod 410 capacity factor ($K^1$) calculated on the Br— anion peak, $K^1$ = 1,39 | | | |

$^1$H-NMR:

Varian 300 MHz ($CDCl_3$) δ (p.p.m.): 0.94 (3H,t,($CH_2CH_3$);

1.37 (2H,m,$CH_2CH_3$); 1.62 (2H,m, $OCH_2$ $CH_2$);

2.15 (3H,s,$CH_3COO$); 2.97 (2H,m,$CH_2COO$); 3.50 (9H,s,+N($CH_3)_3$);

4.10–4.40 (2H,m,$CH_2N$); 4.16 (2H,t,$OCH_2CH_2$);

4.66 (2H,sist.AB,$OCH_2COO$); 5.72(1H,s,CHOCO).

EXAMPLE 13

Preparation of the ester of propionyl L-carnitine bromide with n-butyl glycolate (ST 787).

The title compound was prepared as described in Example 11, utilizing propionyl L-carnitine inner salt.

Physico-chemical properties.

$[\alpha]^{25}_D = -19,6°$ (C=1 in $H_2O$)

TLC: as in Example 1.

Elementary analysis

| calc. % | C 46.61 | H 7.33 | Br 19.38 | N 3.40 |
|---|---|---|---|---|
| found % | C 46.52 | H 7.42 | Br 19.27 | N 3.39 |
| HPLC Waters: | spherisorb column-C1 (5μ), inner diameter = 4 mm length = 125 mm mobile phase $KH_2PO_4$ 50 mM/$CH_3CN$ 70:30, t = 35° C. flow rate: 0,5 ml/min detector R.I. mod 410 Capacity factor ($K^1$) calculated on the Br— anion peak, $K^1$ = 2,07 | | | |

$^1$H-NMR:

Varian 300 MHz ($D_2O$ ) δ (p.p.m.): 0.92 (3H,t,($CH_2CH_3$);

1.10 (3H,t,$CH_3CH_2CO$); 1.36 (2H,m,$CH_2$ $CH_3$); 1.65 (2H,m,$OCH_2CH_2$);

2.48 (2H,q,$CH_3CH_2COO$); 3.00 (2H,d,$CH_2COO$); 3.20 (9H,s,+N $CH_3)_3$);

3.68–4.01 (2H,m,$CH_2N$); 4.23 (2H,t,$OCH_2CH_2$); 4.78 (2H,sist.AB,$OCH_2COO$); 5.74 (1H,m,CHOCO).

EXAMPLE 14

Preparation of the ester of isobutyryl L-carnitine bromide with n-butyl glycolate (ST 762).

The title compound was prepared as described in Example 11, utilizing isobutyryl L-carnitine inner salt.

Physico-chemical properties.

$[\alpha]^{25}_D = -16,7°$ (C=1 in $H_2O$)

TLC: as in Example 1.

Elementary analysis ($C_{17}H_{32}BrN_6$) M.W. 426.36

| calc. % | C 47.89 | H 7.57 | Br 18.74 | N 3.29 |
|---|---|---|---|---|
| found % | C 47.72 | H 7.57 | Br 18.66 | N 3.33 |
| HPLC Waters: | spherisorb column-RP1 (5μ), inner diameter = 4 mm length = 125 mm mobile phase $KH_2PO_4$ 50 mM/$CH_3CN$ 60:40, t = 25° C. flow rate: 1 ml/min detector R.I. mod 410 capacity factor ($K^1$) calculated on the Br— anion peak, $K^1$ = 2,96 | | | |

$^1$H-NMR:

Varian 300 MHz ($CDCl_3$) δ (p.p.m.): 0.92 (3H,t,($CH_3CH_2$);

1.16 (6H, d,CH($CH_3)_2$); 1.36 (2H,m,$CH_2$ $CH_3$); 1.62 (2H,m,$OCH_2CH_2$);

2.60 (1H,m,CH($CH_3)_2$); 2.97 (2H,m,$CH_2COO$); 3.50 (9H,s,+N $CH_3)_3$);

4.10–4.42 (2H,m,$CH_2N$); 4.12 (2H,t,$OCH_2CH_2$);

4.64 (2H,sist.AB,$OCH_2COO$); 5.73 (1H,m,CHOCO).

EXAMPLE 15

Preparation of the ester of isovaleryl L-carnitine bromide with n-butyl glycolate (ST 763).

The title compound was prepared as described in Example 11, utilizing isovaleryl L-carnitine inner salt.
$[\alpha]^{25}{}_D = -15,3°$ (C=1 in H$_2$O)
TLC: as in Example 1.
Elementary analysis (C$_{18}$H$_{34}$BrNO$_6$) M.W. 440.38

| calc. % | C 49.09 | H 7.78 | Br 18.15 | N 3.18 |
|---|---|---|---|---|
| found % | C 49.19 | H 7.82 | Br 17.99 | N 3.12 |
| HPLC Waters: | spherisorb column-RP1 (5μ), inner diameter = 4 mm length = 125 mm mobile phase KH$_2$PO$_4$ 50 mM/CH$_3$CN 60:40, t = 25° C. flow rate: 1 ml/min detector R.I. mod 410 capacity factor (K$^1$) calculated on the Br— anion peak, K$^1$ = 3,30 | | | |

$^1$H-NMR:
Varian 300 MHz (CDCl$_3$) δ (p.p.m.): 0.90 (3H,t,(CH$_2$CH$_3$);
0.90 (6H,d,CH(CH$_3$)$_2$); 1.32 (2H,m,CH$_2$ CH$_3$); 1.55 (2H,m,CH$_2$CH$_2$O);
2.02 (1H,m,CH(CH$_3$)$_2$); 2.18 (2H,m,CH$_2$CH); 2.88 (2H,m,CH$_2$COO);
3.47 (9H,s,$^+$N CH$_3$)$_3$); 4.03–4.30 (2H,m,CH$_2$N); 4.10 (2H,t,CH$_2$CH$_2$O);
4.60 (2H,sist.AB,OCH$_2$COO); 5.63 (1H,m,CHOCO).

In order to prepare the composition of this invention, at least one of the compounds of the formula (I) is preferably dissolved in water or ethanol initially. The solution thus prepared may be admixed in the conventional manner with :commonly available ointment bases such as hydrophilic ointment (USP) or petrolatum (USP).

The water or ethanol used to dissolve the compounds according to this invention may range in concentration of from 1 to 30%, by volume, of the total composition.

The compounds of this invention may also be formulated in a solution or lotion form.

For instance, a compound of the formula (I) is dissolved directly in a mixture of water, ethanol and propylene glicol (40:40:20 by weight).

Some examples of formulation are hereinbelow described:

Formulation 1: 5% solution 5 grams of the compound of example 1 were dissolved in 5 mL of water and the resulting solution admixed with 40 mL of ethanol and 20 mL of propylene glycol. Sufficient water was added to make 100 mL of formulation.

Formulation 2: 5% ointment 5 grams of the compound of example 3 were admixed with 95 grams of USP grade hydrophilic ointment, until a uniform consistency resulted.

We claim:

1. A method of treating dermatosis, comprising topically applying an effective amount of a compound of the formula (I)

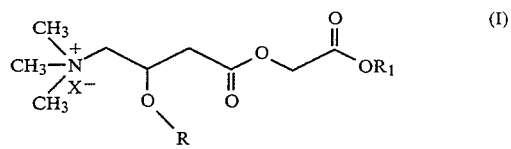

wherein R is hydrogen or straight or branched alkanoyl group having 2–5 carbon atoms;i R$_1$ is hydrogen or straight or branched alkyl group having 1–4 carbon atoms; and X$^-$ is the anion of a pharmacologically acceptable salt, to a patient in need thereof.

2. The method of claim 1, wherein R is acetyl, propionyl, butyryl, isobutyryl, valeryl, or isovaleryl.

3. The method of claim 1, wherein R$_1$ is methyl, n-butyl, or tert-butyl.

4. The method of claim 1, wherein said dermatosis is selected from the group consisting of ichthyosis, psoriasis, dandruff, acne, palmar hyperkeratosis, and plantar hyperkeratosis.

5. A method of treating dermatosis, comprising topically applying an effective amount of a compound of the formula (I')

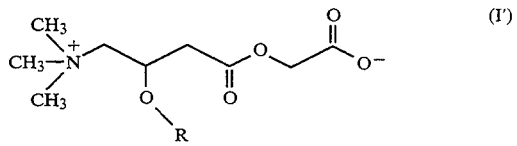

wherein R is hydrogen or straight or branched alkanoyl group having 2–5 carbon atoms 6. The method of claim 5, wherein said dermatosis is ichthyosis, psoriasis, dandruff, acne, palmar hyperkeratosis, or plantar hyperkeratosis.

* * * * *